United States Patent
Kendig et al.

(10) Patent No.: US 10,180,359 B2
(45) Date of Patent: Jan. 15, 2019

(54) METHOD AND SYSTEM FOR CALIBRATING THERMAL IMAGING SYSTEMS

(71) Applicant: Microsanj, LLC, Santa Clara, CA (US)

(72) Inventors: Dustin Kendig, Fremont, CA (US); Ali Shakouri, West Lafayette, IN (US); Hamid Piroozi, Fishers, IN (US)

(73) Assignee: MICROSANJ, LLC, Santa Clara, CA (US)

(*) Notice: Subject to any disclaimer, the term of this patent is extended or adjusted under 35 U.S.C. 154(b) by 0 days.

(21) Appl. No.: 15/881,757

(22) Filed: Jan. 27, 2018

(65) Prior Publication Data

US 2018/0217004 A1   Aug. 2, 2018

Related U.S. Application Data

(60) Provisional application No. 62/451,751, filed on Jan. 29, 2017.

(51) Int. Cl.
| | | |
|---|---|---|
| *G01D 18/00* | (2006.01) | |
| *G01J 5/08* | (2006.01) | |
| *G01J 5/00* | (2006.01) | |
| *G01N 21/17* | (2006.01) | |

(52) U.S. Cl.
CPC ........... *G01J 5/0859* (2013.01); *G01J 5/0003* (2013.01); *G01J 5/0809* (2013.01); *G01N 21/1717* (2013.01); *G01J 2005/0048* (2013.01)

(58) Field of Classification Search
CPC .............. G01N 21/1717; G01N 21/55; G01N 2021/1731; G01N 25/18; G01N 2201/0612; G01N 25/72; G01J 5/0003; G01J 5/0896; G01J 2005/0048; G01J 3/2823

USPC ....................................................... 250/252.1
See application file for complete search history.

(56) References Cited

U.S. PATENT DOCUMENTS

| | | | | |
|---|---|---|---|---|
| 6,940,592 | B2* | 9/2005 | Borden ................ | G01N 21/274 250/559.27 |
| 7,444,260 | B2* | 10/2008 | Raad .................... | G01K 11/125 702/130 |
| 2002/0131476 | A1* | 9/2002 | Baba ..................... | G01K 11/00 374/161 |
| 2006/0274151 | A1* | 12/2006 | Lueerssen ............. | G01J 5/0003 348/180 |
| 2008/0082288 | A1* | 4/2008 | Raad .................... | G01K 11/125 702/130 |

(Continued)

*Primary Examiner* — Taeho Jo

(57) ABSTRACT

A method for determining change in temperature of different parts of an electronic or optoelectronic device between un-energized and energized states without contacting the device. The method includes establishing a reference image form an unexcited device by illuminating the device with an optical signal and capturing the reference image from the device in an un-energized state, illuminating the device with an optical signal during an energization pulse having a predetermined pulse width and pulse magnitude and capturing a plurality of on images from the device at different time delays, determining a transient temperature profile, calibrating the temperature profile for one or more regions of the device with unknown thermoreflectance coefficient based on the determined transient temperature profile for the one or more regions of the device with known thermoreflectance coefficient.

6 Claims, 6 Drawing Sheets
(2 of 6 Drawing Sheet(s) Filed in Color)

(56) References Cited

U.S. PATENT DOCUMENTS

| | | | | |
|---|---|---|---|---|
| 2009/0297017 | A1* | 12/2009 | Hudgings | G06T 7/0008 382/141 |
| 2013/0301676 | A1* | 11/2013 | Chang | G01J 5/0003 374/137 |
| 2013/0340127 | A1* | 12/2013 | Wu | G01Q 60/58 850/50 |
| 2015/0110150 | A1* | 4/2015 | Schmidt | G01N 21/1717 374/43 |
| 2015/0316496 | A1* | 11/2015 | Chang | H01L 22/12 374/5 |
| 2017/0299440 | A1* | 10/2017 | Chang | G01J 5/10 |

* cited by examiner

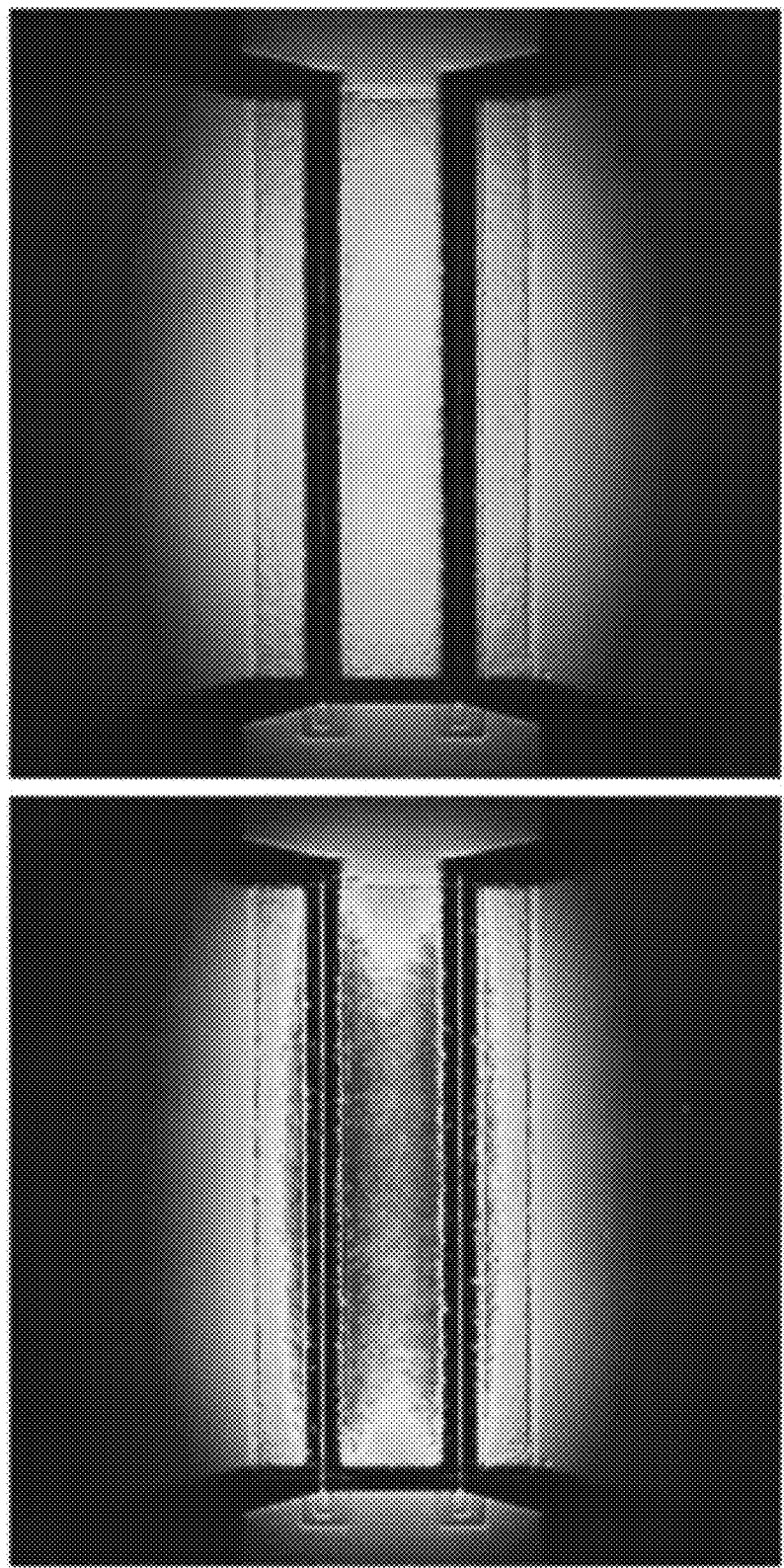

METHOD AND SYSTEM FOR CALIBRATING THERMAL IMAGING SYSTEMS

CROSS-REFERENCE TO RELATED APPLICATIONS

The present U.S. patent application is related to and claims the priority benefit of U.S. Provisional Patent Application Ser. No. 62/451,751, filed 29 Jan. 2017, the contents of which is hereby incorporated by reference in its entirety into the present disclosure.

TECHNICAL FIELD

The present application relates to non-contact thermal measurements, and more particularly to thermoreflectance based measurement methods and systems.

BACKGROUND

This section introduces aspects that may help facilitate a better understanding of the disclosure. Accordingly, these statements are to be read in this light and are not to be understood as admissions about what is or is not prior art.

The field of non-contact thermal imaging is associated with a variety of applications, e.g., measuring thermal characteristics of an electronic device under test. Thermal imaging using thermoreflectance has received attention in recent years. Thermoreflectance-based imaging is dependent on the measurement of the relative change in the sample's surface reflectivity as a function of temperature. As the temperature of a sample changes, the refractive index, and therefore, the reflectivity also changes. The change in reflectivity is dependent on the Thermoreflectance Coefficient, a basic material property that is a function of the imaging system's numerical aperature, illumination wavelength, the sample material and material surface characteristics, and the ambient temperature. U.S. Pat. No. 7,173,245 to Shakouri et al., incorporated by reference in its entirety into the present disclosure, describes an example of such systems and methods.

In one method, an optical signal can be used to illuminate an electronic or optoelectronic device between un-energized and energized states without contacting the device in order to interrogate thermal behavior of the device when energized. Such thermal interrogation, however, requires knowledge of thermoreflectance coefficients for various parts of the device. While the thermoreflectance coefficient of one or more parts of the device may be known, such knowledge may be lacking for other parts of the device.

There is, therefore an unmet need for a novel method and system that can interrogate thermal behavior of an electronic or optoelectronic device with a known thermoreflectance coefficient of one or more regions but with unknown thermoreflectance coefficients of one or more other regions.

SUMMARY

A method for determining change in temperature of different parts of an electronic or optoelectronic device between un-energized and energized states without contacting the device. The method includes establishing a reference image form an unexcited device by illuminating the device with an optical signal and capturing the reference image from the device in an un-energized state. The method further includes illuminating the device with an optical signal during an energization pulse having a predetermined pulse width and pulse magnitude and capturing a plurality of on images from the device at different time delays. In addition, the method includes determining a corresponding transient temperature profile for one or more regions of the device with known thermoreflectance coefficient based on the plurality of on images and the reference image. The method also includes determining a corresponding relative temperature profile of one or more regions of the device with unknown thermoreflectance coefficient based on the plurality of on images and the reference image. Furthermore, the method includes calibrating the temperature profile for the one or more regions of the device with unknown thermoreflectance coefficient based on the determined transient temperature profile for the one or more regions of the device with known thermoreflectance coefficient.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3A is a thermoreflectance image of a gate-drain-source structure at time 10 µs right after an energization cycle has ended.

FIG. 3B is the same gate-drain-source structure shown in FIG. 3A, shown at time 20 µs (i.e. 10 µs after the energization cycle has ended).

DETAILED DESCRIPTION

Figure 1:
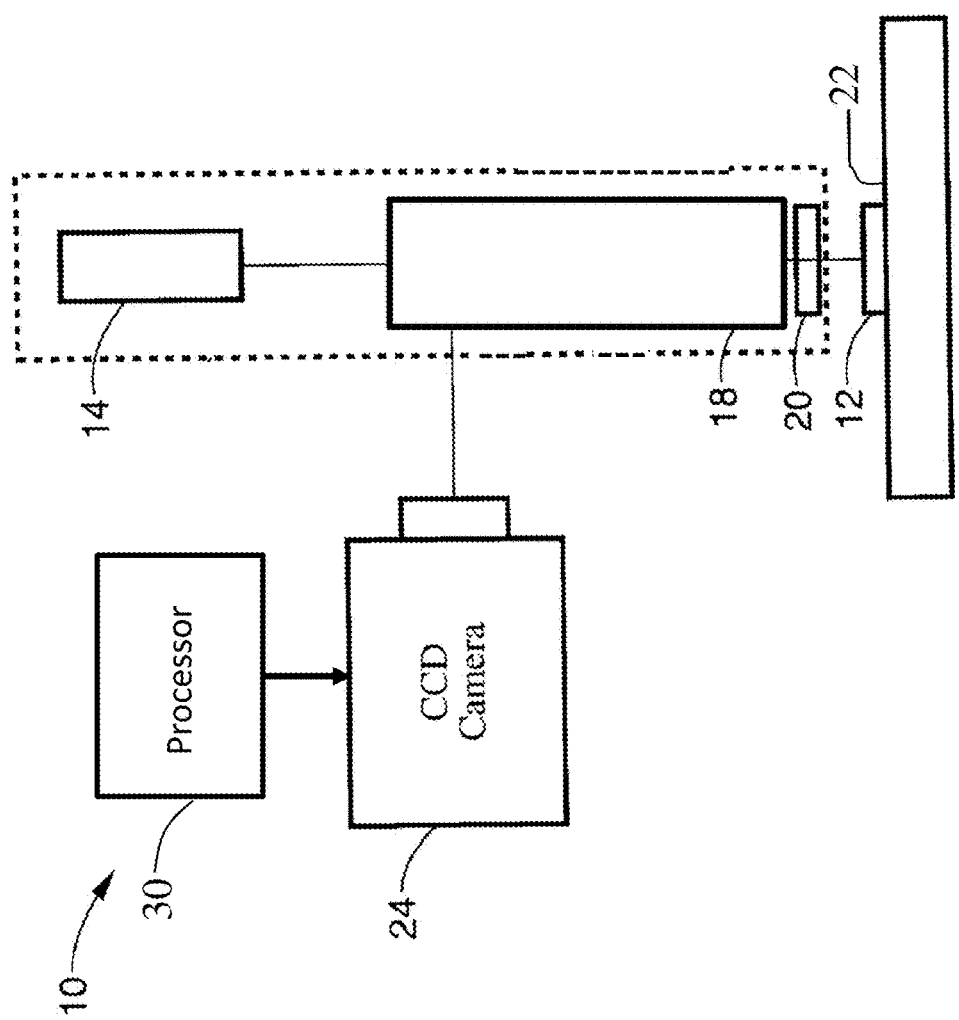
FIG. 1 is a schematic of a thermoreflectance imaging system including an x-y translation stage on which a sample is placed.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

A new method and system for interrogating thermal behavior of an electronic or optoelectronic device with a known thermoreflectance coefficient of one or more regions but with unknown thermoreflectance coefficients of one or more other regions is presented. Material calibration for devices with submicron features is a challenge for many thermal imaging techniques due to thermal expansion and sample movement. Thermoreflectance is a sensitive thermal measurement technique that uses illumination, e.g., in the visible wavelength range to obtain thermal measurements with a resolution of 0.2 μm or less. The thermoreflectance effect is typically 1 part in 10,000 per ° C. temperature change, therefore any small change in light intensity due to even a few tens of nanometers of thermal expansion or vibration can cause large false thermal signals. In the present disclosure, a method and a system are disclosed for obtaining reliable thermal data for small features even with these obstacles by using short-timescale transient thermal data close to the device regions of interest.

Referring to FIG. 1, a system 10 for thermoreflectance imaging is depicted. An illumination source is provided by laser or light emitting diode (LED) 14 whose light beam is directed onto sample 12 through optical components 18, and an objective lens 20, which are all preferably located on an x-y translation stage 22. The x-y translation stage is configured to position the sample 12 according to a set of coordinates and to set the temperature of the stage 22. The reflected light is therefore send to an imager, exemplified as CCD camera 24, or other photo detectors known to a person having ordinary skill in the art. The use of CCD camera 24 within the setup allows optical positioning of the illumination, such as the spot from the laser beam, onto sample 12 while viewing the sample under test. The CCD camera 24 is in turn coupled to a processor 30 configured to control activation of the sample 12, the CCD camera 24, the x-y translation stage (both position and its temperature) and processing, as described below. The laser or LED 14 can be a semiconductor type, e.g. from THORLABS, operating at ranges from about 350 nm to about 2000 nm. The laser or LED 14 can be operating at ranges from about 1 mW to about 100 mW.

According to the teachings of the present disclosure a method is described that addresses the shortcomings of the prior art, particularly challenges associated with calibrating on small features of the device under test (DUT) due to sample movement during the stage thermal expansion.

Figure 2:
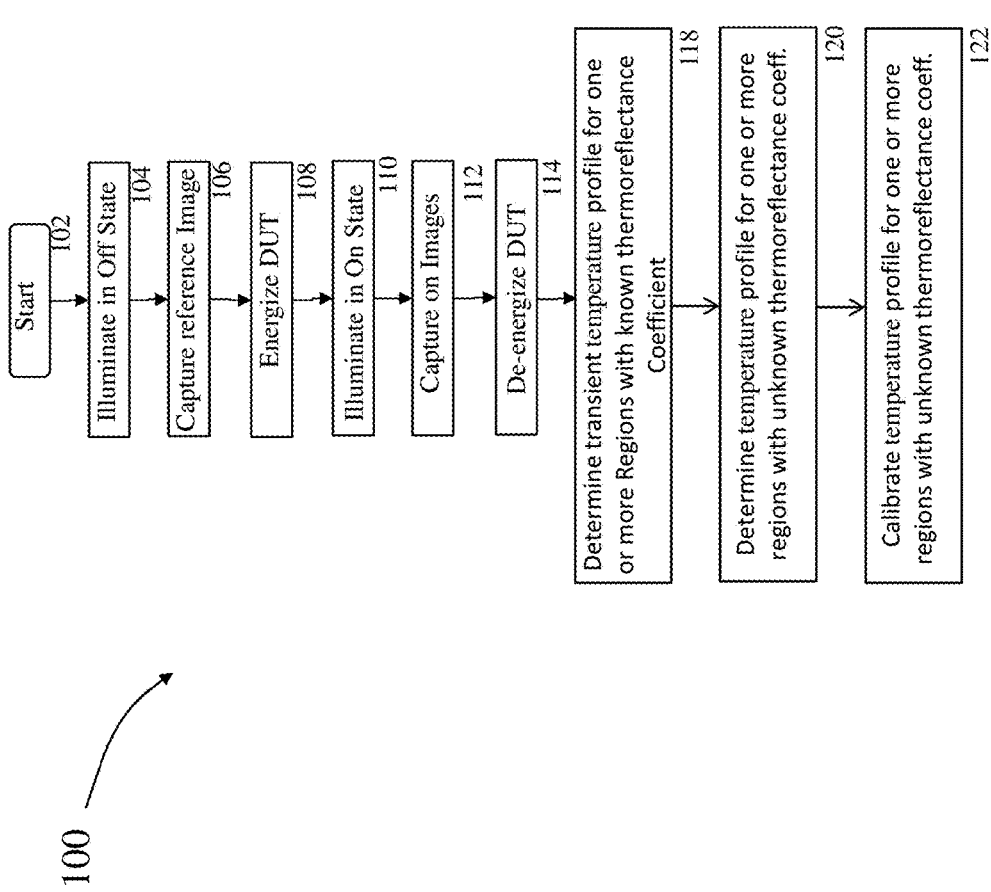
FIG. 2 is a flow chart listing the steps according to the method of the present disclosure.

Referring to FIG. 2, a flow chart 100 is provided depicting steps in calibrating the system 10 for thermoreflectance imaging. The flow chart 100 starts at block 102. In block 104, the processor 30 (see FIG. 1) illuminates the DUT with an optical signal with the DUT in the off state. Actions described in the flow chart 100 are typically commanded by the processor 30 in connection with other peripheral devices such as the CCD camera 24, or other peripheral devices discussed herein. In block 106, one or more reference images are captured. In block 108 the DUT is energized by providing a pulse with a predetermined pulse width and magnitude to the DUT. This state constitutes the "on state" of the DUT. In block 110, the DUT is illuminated with an optical signal while the device is in the on state. In block 112, one or more images are captured representing images of the DUT in the on state. In block 114, the DUT is de-energized. Steps in blocks 108-114 may be repeated a plurality of times for purpose of averaging images in the on state. In block 118, a corresponding transient temperature profile for one or more regions of the device with known thermoreflectance coefficient is (are) determined based on the plurality of on images and the reference image captured in block 106.

The processor 30 computes the thermoreflectance coefficient $C_{TR}$ based on the relationship provided in equation 1 and by changing the temperature of the stage 22 between $T_{high}$ and $T_{low}$.

$$\frac{\Delta R}{R} = \frac{R_{high}(x, y, \lambda) - R_{low}(x, y, \lambda)}{R_{low}(x, y, \lambda)} = C_{TRi}(x, y, \lambda)(T_{high} - T_{low}), \quad (1)$$

wherein $R_{high}$ (x,y,λ)–$R_{low}$(x,y,λ) is the difference between the high and low temperature reflectance images for a plurality of pixels in a grid measured in x and y for a wavelengths λ for regions with known or assumed known thermoreflectance coefficient ($C_{TR}$(x,y,λ)). The ranges for wavelengths λ are between about 350 nm to about 2000 nm. The range of temperature $T_{low}$ is between about 10° C. and about 50° C. The range of temperature $T_{high}$ is between about 20° C. and about 200° C. The difference between $T_{high}$ and $T_{low}$ ranges between about 10° C. and 190° C.

In block 120, a corresponding relative temperature profile of one or more regions of the device with unknown thermoreflectance coefficient based on the plurality of on images and the reference image is (are) determined, using the same thermoreflectance coefficient of the nearby region with the known thermoreflectance coefficient.

Finally in block 122 the temperature profile determined in block 120 is (are) calibrated based on the transient temperature profile for the one or more regions of the device with known thermoreflectance coefficient, as determined in block 118.

In one embodiment, the step of calibration (block 122) is performed by scaling the temperature profile of the one or more regions of the device with unknown thermoreflectance coefficient such that a predetermined time after the end of the energization pulse (i.e., block 114), the transient temperature profiles are aligned.

Using this method, in one embodiment, the unknown thermoreflectance coefficient(s) of nearby regions can be calculated for use in further calibrating and confirming the true temperature profile of other regions according to Equation 2.

$$C_{TR}(x, y, \lambda) = \frac{R_{high}(x, y, \lambda) - R_{low}(x, y, \lambda)}{R_{low}(x, y, \lambda)} \cdot \frac{1}{T_{high} - T_{low}}, \quad (2)$$

wherein $C_{TR}$(x,y,λ) is the calculated thermoreflectance coefficient for $R_{high}$ (x,y,λ)–$R_{low}$(x,y,λ) (the difference between the high and low temperature reflectance images for a plurality of pixels in a grid measured in x and y for a wavelengths λ for regions with unknown thermoreflectance coefficient). The calculated thermoreflectance coefficient for the unknown regions can then be used to calculate ΔR/R (as per Equation 1) to obtain temperature profile for the difference between the high and low temperature reflectance images for a plurality of pixels in a grid measured in x and y for a wavelengths λ for other regions with similar structures with the calculated thermoreflectance coefficient ($C_{TR}$(x,y,λ)).

Referring to FIG. 3A, a gate-drain-source structure is shown at time 10 μs right after an energization cycle has ended. Referring to FIG. 3B, the same gate-drain-source structure is shown at time 20 μs (i.e. 10 μs after the energization cycle has ended). FIGS. 3A and 3B illustrate how the temperature profile changes when the device is turned off. When the device is turned off, temperature on top of the device becomes uniform and thus extrapolation/continuity is evident.

In the present disclosure, it is assumed the thermal profile is uniform over short distances shortly after device excitation is turned off from an on state depending on the thermal diffusion time of the material and distance of interest. Some examples are shown in table 1 (below); e.g., if a large drain pad on a Si substrate is 10 μm away, one can assume that ~0.284 μs after the excitation has turned off, the heat would diffuse and be relatively uniform at that distance.

Following this, heat begins to transfer into the substrate as can be seen in the transient data (the gate heats up in a few microseconds and the drain and source are slightly behind). This increase of substrate temperature is similar to increasing the ambient temperature with a thermal chuck. It is desirable for the heat to spread in the substrate so that areas

| Diffusion Time Estimations | SiO$_2$ | Si | Cu | Diamond (600 W/mK) | Diamond (2000 W/mK) | 3C—SiC | 4H—SiC | 6H—SiC | Au |
|---|---|---|---|---|---|---|---|---|---|
| Thermal diffusivity: α (m$^2$/s) | 8.30E−07 | 8.80E−05 | 1.11E−04 | 3.00E−04 | 1.10E−03 | 1.60E−04 | 1.70E−04 | 2.20E−04 | 1.27E−04 |
| Thickness (μm) | | | | Diffusion time (μs) | | | | | |
| 1 | 0.301 | 0.003 | 0.002 | 0.001 | 0.000 | 0.002 | 0.001 | 0.001 | 0.002 |
| 5 | 7.530 | 0.071 | 0.056 | 0.021 | 0.006 | 0.039 | 0.037 | 0.028 | 0.049 |
| 10 | 30.12 | 0.284 | 0.225 | 0.083 | 0.023 | 0.156 | 0.147 | 0.114 | 0.197 |
| 25 | 188.3 | 1.776 | 1.408 | 0.521 | 0.142 | 0.98 | 0.92 | 0.71 | 1.230 |
| 50 | 753.0 | 7.10 | 5.63 | 2.08 | 0.57 | 3.91 | 3.68 | 2.84 | 4.92 |

Figure 3C:
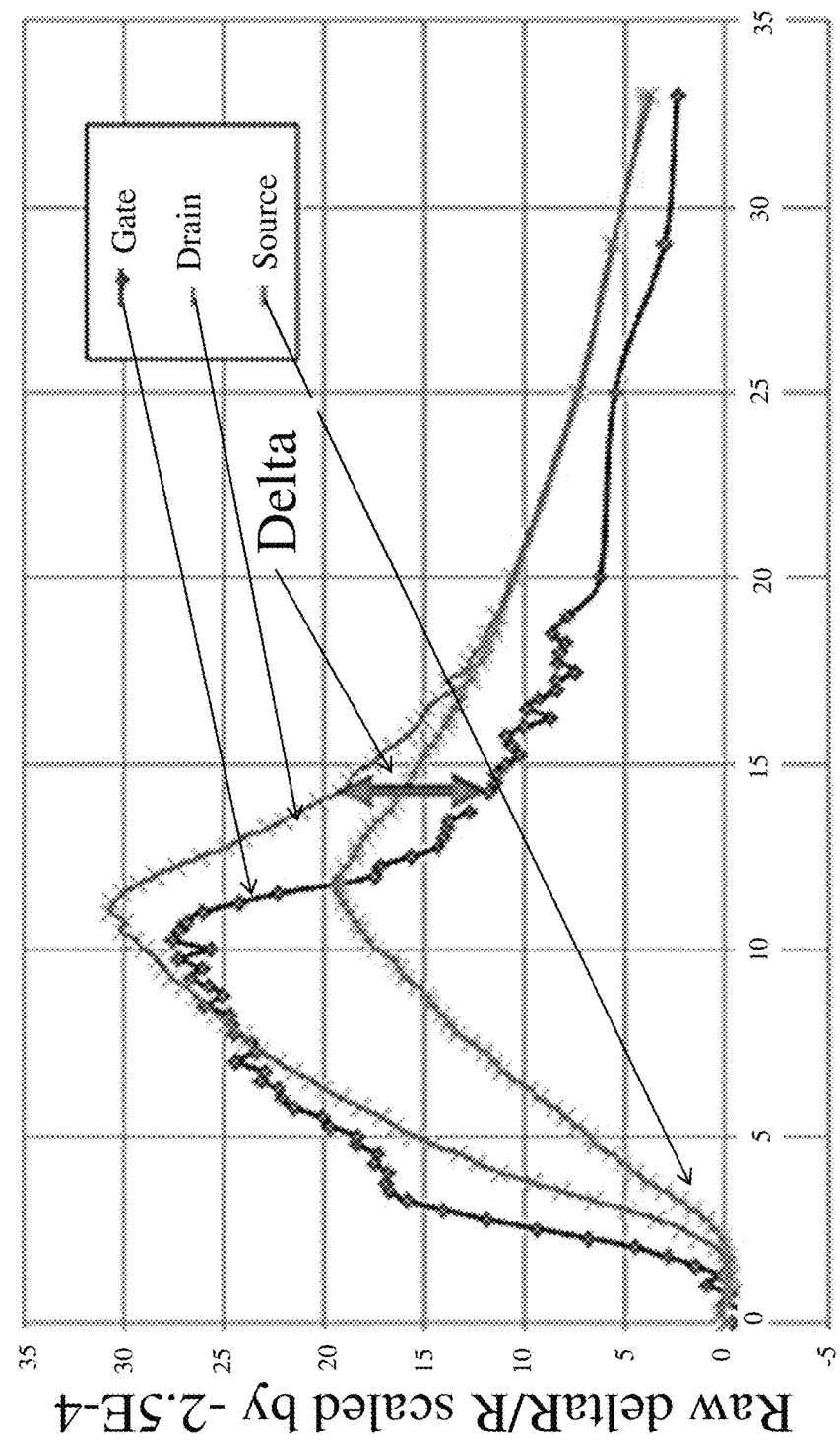
FIG. 3C is a graph of raw data for $\Delta R/R$ where $\Delta R$ is the difference between the high and low temperature reflectance images for a plurality of pixels in a grid as a function of time in µs.
Figure 3D:
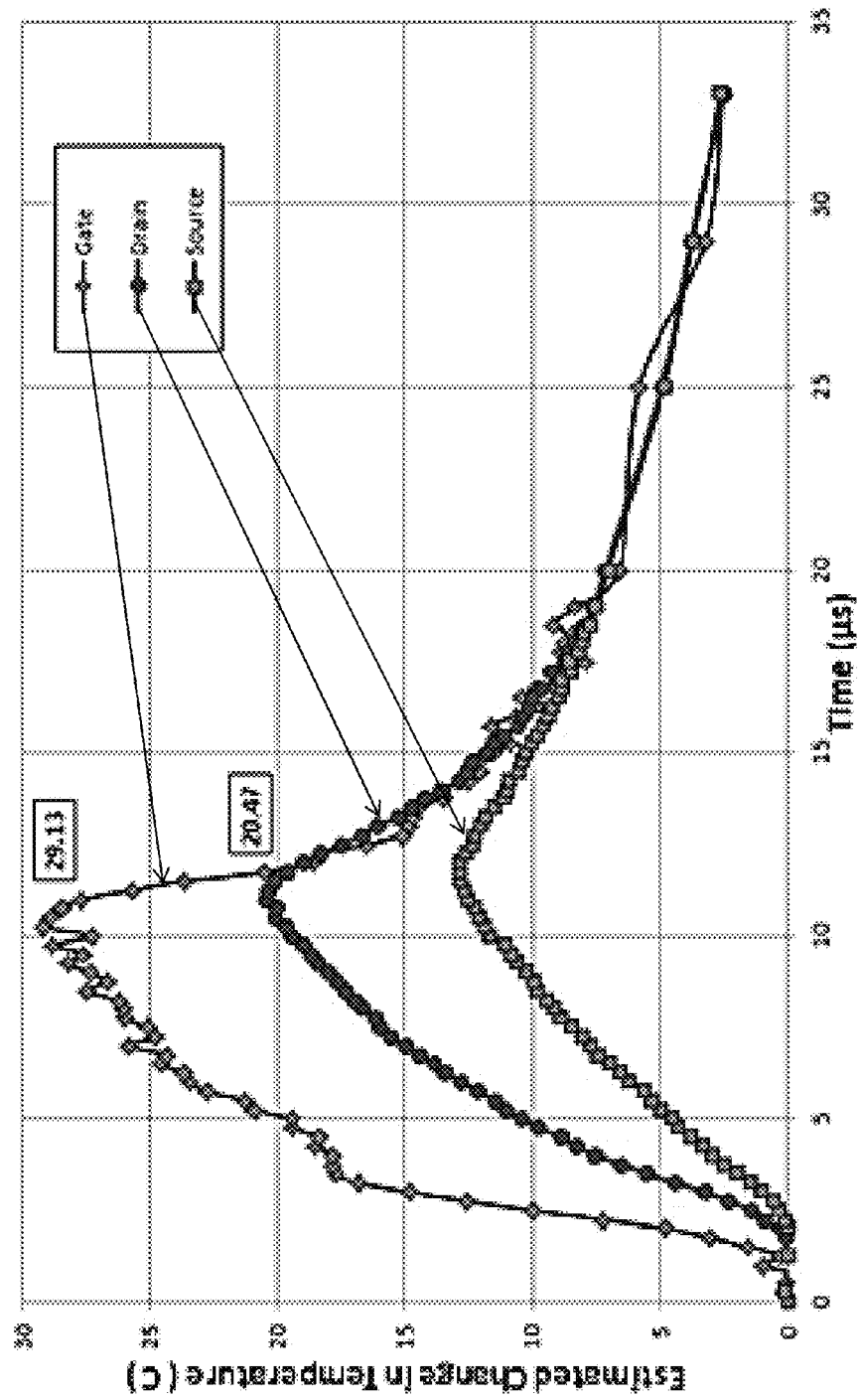
FIG. 3D is graph of estimated temperature change in ° C. vs. time in µs including adjusted thermoreflectance coefficients.

Referring to FIG. 3C raw data for the gate-drain-source structure shown in FIGS. 3A and 3B using the same thermoreflectance coefficient −2.5E-4 (standard thermoreflectance coefficient for unpassivated gold) for gate, source, and drain regions are shown. This data shows the gate is cooler at 10 μs than the drain, and after the power is turned off, the gate region seems to cool down faster than the drain and source. This difference is due to a difference in the $C_{th}$ for the gate and drain region. This difference is due to material or passivation layer thickness differences. It should be noted that thermal decay data for the source and drain regions reach the same temperature at ~17 μs after the energization pulse since they have the same $C_{th}$. In FIG. 3C, the difference between the thermal profiles of the gate and drain at about 14 μs is expressed as an arrow denoted as Delta. Based on the substrate thermal diffusivity and the distance between the gate and the drain, these two locations should be at the same temperature at about 14 μs (4 μs after the device has been turned off). Referring to FIG. 3D, estimated temperature rise with adjusted thermoreflectance coefficient by scaling the gate temperature profiles with respect to the drain and source temperature profile by the distance of the arrow Delta is shown.

Thermal expansion at longer time scales, greater than ~100 μs, can cause pixel by pixel data to be subject to artifacts or "edge effects" on small, sharp features. Larger and more uniform regions are less affected by this and thus can be used to relate the long time-scale data for these regions to the short time-scale data for small regions. The change in temperature between the larger regions (drain) and smaller regions (gate) will remain constant unless large changes in thermal conductivity occur due to increased substrate temperatures. Typically, thermal conductivity will decrease with increasing temperature. Changes in thermal conductivity can be determined by obtaining short timescale transient thermal measurements at different ambient temperature, e.g., determining the gate temperature change due to a 10 μs pulse at 25° C. and 90° C. stage temperature. With the power to the DUT on, temperature fields will be non-uniform. Only when the power to the device has been turned off will heat spread and become uniform over time. When short time pulses are applied, the different thermal resistances between the Gate and the substrate can be determined. The gate region, being small and close to the heat source (channel of the transistor), will heat up very quickly.

close by can be referenced, however, excessive heating of the DUT can result in thermal expansion which can cause the ROI to shift or go out of focus. At high magnifications (~50×-100×) the focal depth is ~0.8 um, so if thermal expansion causes the region of interest (ROI) to defocus even by a small amount it will affect the thermoreflectance results. At lower magnification the depth of focus is in mm range, so thermal expansion is not as much of an issue. Since the initial goal is to search for changes of 1 part in 10,000 in the thermoreflectance, if the change in focus alters the amount of light received by the camera by even a small amount, it can cause an artificial thermal signal. According to one embodiment, 90° C. can be chosen to simulate the thermal conductivity change in the substrate when the device is at steady state. At DC the substrate will heat up and have lower thermal conductivity. Therefore, heating from a 10 μs pulse is expected to be lower at 25 C stage temperature than at 90° C.

Figure 4:
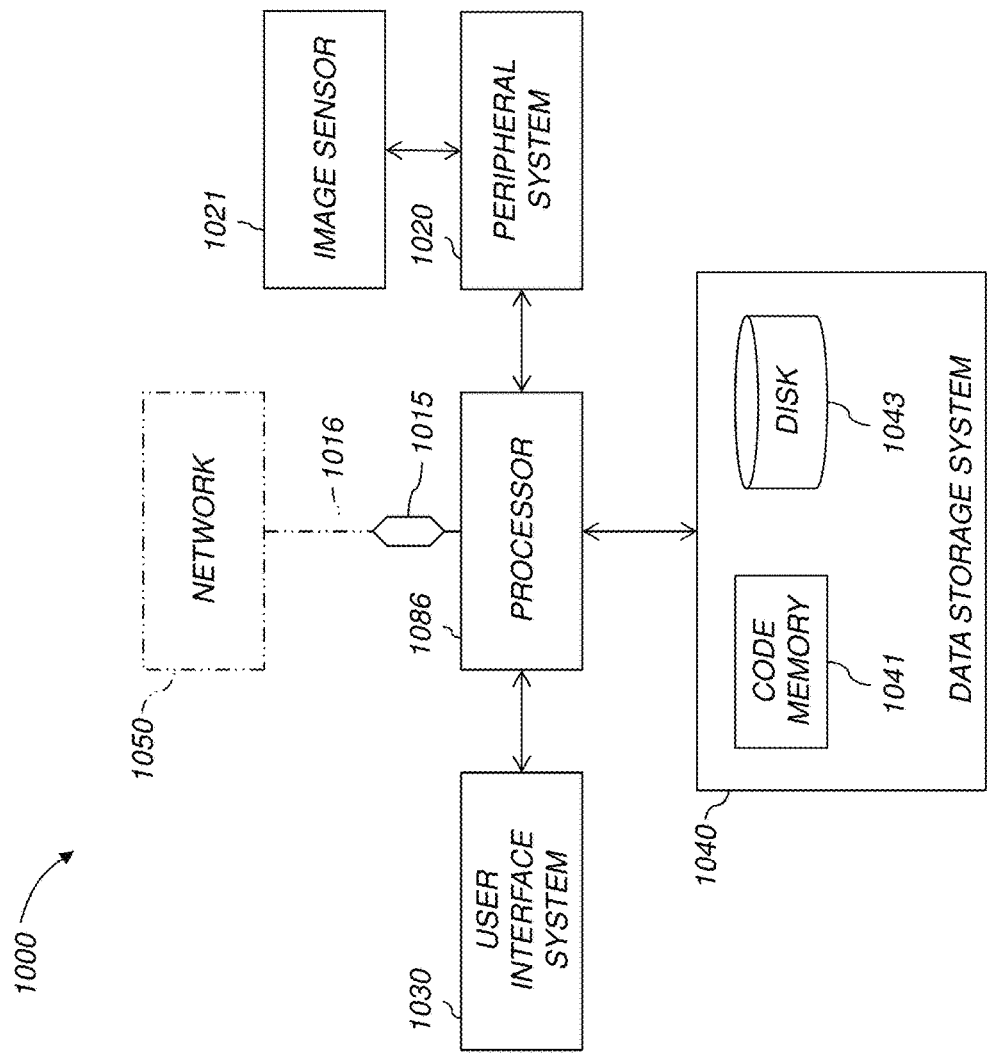
FIG. 4 is a high-level diagram showing the components of an exemplary data-processing system 1000 for analyzing data and performing other analyses described herein, and related components.

Referring to FIG. 4, a high-level diagram showing the components of an exemplary data-processing system 1000 for analyzing data and performing other analyses described herein, and related components. The system includes a processor 1086 (identified as 30 in FIG. 1), a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The imaging described in the present disclosure may be obtained using imaging sensors 1021 and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1086 can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 1086 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (connected, e.g., via a network or a null-modem cable), or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors), to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

Those skilled in the art will recognize that numerous modifications can be made to the specific implementations described above. The implementations should not be limited to the particular limitations described. Other implementations may be possible.

The invention claimed is:

1. A method for determining change in temperature of different parts of an electronic or optoelectronic device between un-energized and energized states without contacting the device, comprising:

establishing a reference image form an unexcited device by illuminating the device with an optical signal and capturing the reference image from the device in an un-energized state;

illuminating the device with an optical signal during an energization pulse having a predetermined pulse width and pulse magnitude and capturing a plurality of on images from the device at different time delays;

determining a corresponding transient temperature profile for one or more regions of the device with known thermoreflectance coefficient based on the plurality of on images and the reference image;

determining a corresponding relative temperature profile of one or more regions of the device with unknown thermoreflectance coefficient based on the plurality of on images and the reference image; and calibrating the temperature profile for the one or more regions of the device with unknown thermoreflectance coefficient based on the determined transient temperature profile for the one or more regions of the device with known thermoreflectance coefficient.

2. The method of claim 1, further comprising calculating the thermoreflectance coefficient of the one or more regions with unknown thermoreflectance coefficient using the calibrated temperature profile.

3. The method of claim 2, further comprising determining a corresponding temperature profile of one or more regions of the device with the calculated thermoreflectance coefficient based on the plurality of on images and the reference image.

4. The method of claim 1, the step of calibrating is by scaling the relative temperature profile of the one or more regions of the device with unknown thermoreflectance coefficient such that a predetermined time after the end of the energization pulse, the temperature profiles are scaled to the transient temperature profile for the one or more regions with known thermoreflectance coefficient.

5. The method of claim 4, further comprising calculating the thermoreflectance coefficient of the one or more regions with unknown thermoreflectance coefficient using the calibrated temperature profile.

6. The method of claim 5, further comprising determining a corresponding temperature profile of one or more regions of the device with the calculated thermoreflectance coefficient based on the plurality of on images and the reference image.

* * * * *